(12) United States Patent
Schneider

(10) Patent No.: US 7,612,763 B2
(45) Date of Patent: Nov. 3, 2009

(54) COMPUTER PERIPHERAL WITH INTEGRATED INFRARED THERAPY AND METHOD OF MAKING SAME

(75) Inventor: Paul P. Schneider, Bayside, WI (US)

(73) Assignee: Schneider Data Technologies, Bayside, WI (US)

( * ) Notice: Subject to any disclaimer, the term of this patent is extended or adjusted under 35 U.S.C. 154(b) by 593 days.

(21) Appl. No.: 11/462,217

(22) Filed: Aug. 3, 2006

(65) Prior Publication Data

US 2008/0030457 A1    Feb. 7, 2008

(51) Int. Cl.
G09G 5/08    (2006.01)
(52) U.S. Cl. ...................................... 345/163
(58) Field of Classification Search .......... 345/156–167
See application file for complete search history.

(56) References Cited

U.S. PATENT DOCUMENTS

| | | | |
|---|---|---|---|
| 5,527,350 A | 6/1996 | Grove | |
| 5,828,034 A | 10/1998 | Chang | |
| 5,854,621 A * | 12/1998 | Junod et al. | 345/158 |
| 6,063,108 A | 5/2000 | Salansky | |
| 6,510,346 B2 | 1/2003 | Gordon | |
| 6,603,460 B2 * | 8/2003 | Hua-Yung | 345/163 |
| 6,676,654 B1 | 1/2004 | Balle-Petersen | |
| 6,847,846 B2 | 1/2005 | Sun | |
| 6,859,196 B2 * | 2/2005 | Kehlstadt | 345/156 |
| 7,118,563 B2 | 10/2006 | Weckwerth | |
| 2003/0040783 A1 * | 2/2003 | Salmon | 607/111 |
| 2004/0054386 A1 * | 3/2004 | Martin et al. | 607/88 |
| 2005/0065577 A1 | 3/2005 | MacArthur | |
| 2005/0146499 A1 | 7/2005 | Casebolt et al. | |
| 2007/0007399 A1 * | 1/2007 | Cheng et al. | 248/118.1 |
| 2007/0167999 A1 * | 7/2007 | Breden et al. | 607/88 |
| 2008/0046044 A1 * | 2/2008 | Jahnigen et al. | 607/100 |

OTHER PUBLICATIONS

"Phototherapy promotes regeneration and functional recovery of injured peripheral nerve" by Juanita J. Anders, Stefano Geuna and Shimon Rochkind.
Medical College of Wisconsin: Light-Emitting Diodes, Jan. 1999, http://www.mcw.edu/whelan/html/6/index.html.

* cited by examiner

*Primary Examiner*—Richard Hjerpe
*Assistant Examiner*—Tom V Sheng
(74) *Attorney, Agent, or Firm*—Michael P. Mazza, LLC

(57) ABSTRACT

An apparatus for infrared therapy includes a body having a first surface portion and a second surface portion. A motion sensing device is positioned adjacent to the first surface portion and is configured to determine movement of the body, such as a computer mouse, relative to a reference, such as a mouse pad. A plurality of infrared LEDs is positioned adjacent to the second surface portion and is configured to emit infrared light toward a hand of a user.

19 Claims, 4 Drawing Sheets

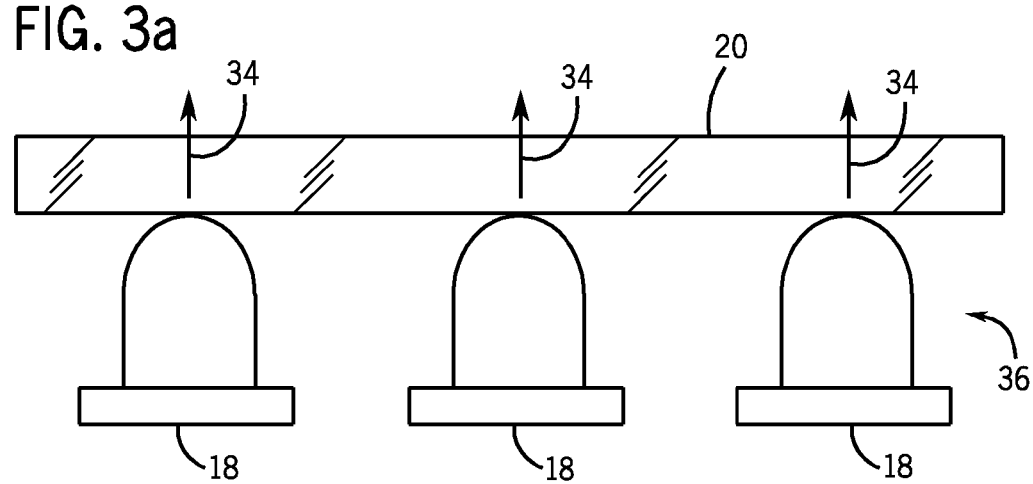
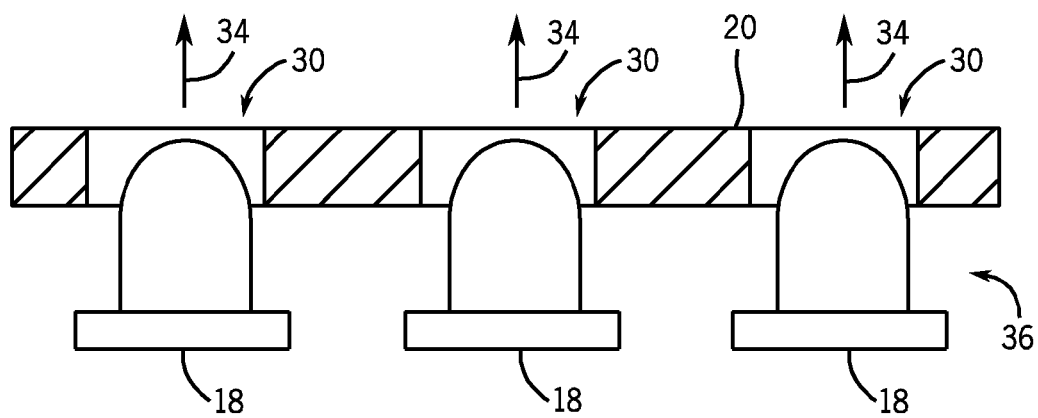

COMPUTER PERIPHERAL WITH INTEGRATED INFRARED THERAPY AND METHOD OF MAKING SAME

BACKGROUND OF THE INVENTION

The present invention relates generally to a computer mouse and, more particularly, to a computer mouse having infrared light therapy.

Computers and other products using computer mice and other pointing devices are commonplace in both the business and personal settings. Typically, a user is required to direct movement of a cursor on a computer screen by physically moving the user's hand to move the mouse or by moving individual fingers to direct movement of a track ball. Repetitive stress injuries and other maladies, such as, arthritis, tendonitis, and carpal tunnel syndrome, may be further inflamed or exacerbated by using a computer mouse.

Light emitting diode (LED) technology is capable of delivering light deep into tissues of the body. Various wavelengths are said to be optimal for pain treatment and wound healing. LED technology has been shown to be helpful in relieving pain and in improving healing. However, therapy of repetitive stress injuries and other maladies described above often requires halting mouse movement while the therapy is applied.

It would therefore be desirable to have an apparatus capable of LED technology therapy while maintaining the ability to use a mouse, or other such computer peripheral, at the same time.

BRIEF DESCRIPTION OF THE INVENTION

The present invention provides an apparatus for promoting healing from repetitive stress injuries that overcomes the aforementioned drawbacks. A hand-held computer peripheral control apparatus, such as a computer mouse, has a motion sensing device for determining movement of the apparatus body relative to a reference point. The apparatus of the present invention also has a plurality of infrared LEDs that emit infrared light toward a user's hand.

In accordance with another aspect of the invention, a hand-manipulated computer peripheral includes a body having a first surface portion and a second surface portion. At least one motion sensing device is positioned adjacent to the first surface portion and is configured to determine movement of the body relative to a reference. The peripheral also includes a plurality of infrared LEDs positioned adjacent to the second surface portion and configured to emit infrared light toward a hand of a user.

In accordance with another aspect of the invention, a method of manufacturing a hand-manipulated computer apparatus includes attaching a movement detection device to a body of a hand-manipulated computer apparatus and configuring the movement detection device to monitor movement of the body relative to a surface. The method also includes attaching a bank of infrared LEDs to the body, and aligning the bank of infrared LEDs to emit infrared light toward a user's hand when the user's hand is positioned to move the body relative to the surface.

According to another aspect, the invention is embodied in a computer system including a computer and a mouse connected to the computer. The mouse includes a body, a movement sensing device positioned adjacent to the body and configured to detect planar translation of the body, and a plurality of infrared LEDs positioned adjacent to the body, each infrared LED oriented to emit infrared light in a direction toward a hand of a user.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 3a is a cross-sectional view along line 3-3 of FIG. 1 according to one embodiment of the present invention.

FIG. 3b is a cross-sectional view along line 3-3 of FIG. 1 according to another embodiment of the present invention.

DETAILED DESCRIPTION OF THE PREFERRED EMBODIMENT

Figure 1:
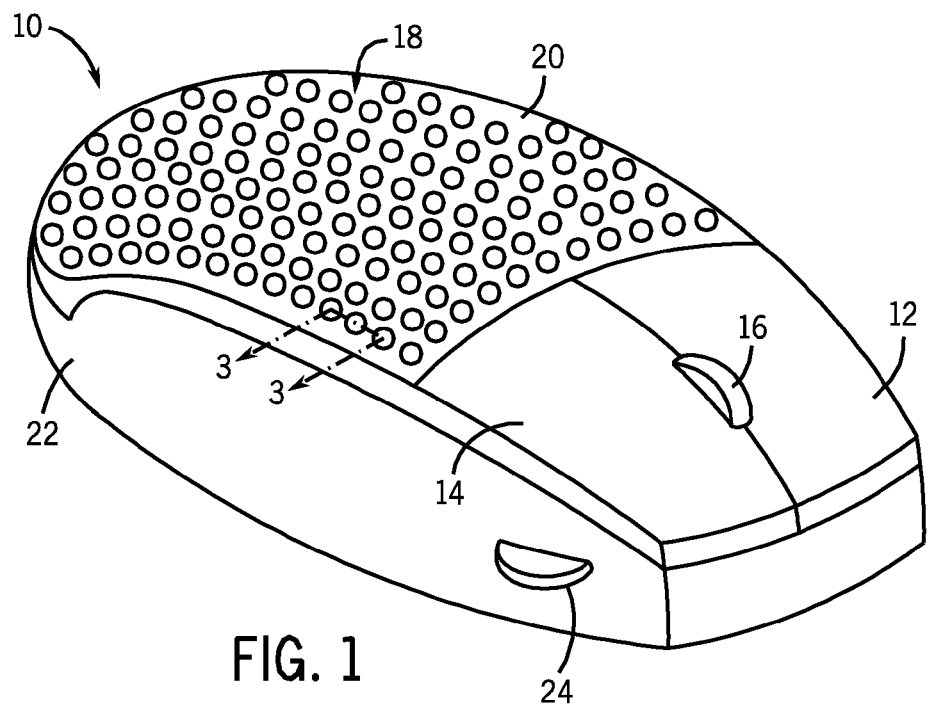
FIG. 1 is a perspective view of a computer peripheral in accordance with one aspect of the present invention.

FIG. 1 shows a hand-held, or hand manipulated computer peripheral or apparatus 10, such as a computer mouse, for controlling a computer cursor (not shown). Peripheral 10 includes a left button 12 and a right button 14 for performing left and right button functions, respectively. Peripheral 10 also includes a scroll wheel 16 for performing scrolling functions and, optionally, middle button functions.

A bank or plurality of infrared LEDs 18 is attached to the peripheral 10. The plurality of infrared LEDs 18 is preferably positioned adjacent to a top portion 20 of a body 22 of the peripheral 10 so as to direct infrared light toward a palm of a user's hand when using the peripheral 10. The plurality of infrared LEDs 18 preferably emits a light wavelength of 880 nm. However, it is contemplated that the plurality of infrared LEDs 18 may include a group of LEDs emitting light at a first wavelength and another group of LEDs emitting light at a second wavelength. Peripheral 10 preferably includes a switch 24 for setting a powered state of the plurality of infrared LEDs 18. Switch 24 may be an analog or a digital switch. Alternatively or in addition to the switch 24, as will be described hereinbelow, a computer program may be provided to set the powered state of the plurality of infrared LEDs 18.

One skilled in the art will recognize that, as the functionality needs and/or shapes change related to computer peripheral technology, the shape of the peripheral and the number of function buttons may vary from that shown in FIG. 1. However, it is contemplated that a computer peripheral having different and/or additional buttons as well as a different shape from that described herein is possible and within the scope of the appending claims.

Figure 2:
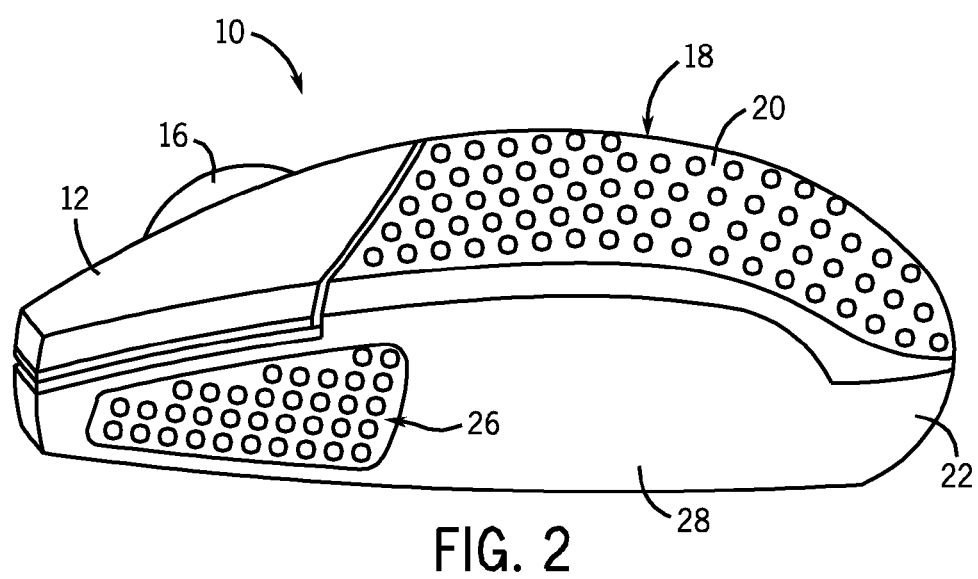
FIG. 2 is a side plan view of the computer peripheral of FIG. 1.

As shown in FIG. 2, peripheral 10 includes a plurality of infrared LEDs 26 positioned adjacent to a side portion 28 of body 22. The plurality of infrared LEDs 26 is positioned so as to direct infrared light toward a thumb of the user's hand when using the peripheral 10.

FIGS. 3a and 3b show a cross-sectional view along line 3-3 of FIG. 1. In one embodiment, as shown in FIG. 3a, at least a portion of top portion 20 is constructed of a material translucent to infrared light 34. The plurality of infrared LEDs 18 is positioned within an interior volume 36 of peripheral 10 and positioned to emit infrared light 34 exterior to peripheral 10.

In another embodiment, as shown in FIG. 3b, a plurality of apertures 30 are formed in top portion 20. The plurality of infrared LEDs 18 are aligned with the plurality of apertures 30 and may extend into or through the plurality of apertures 30.

Figure 4:
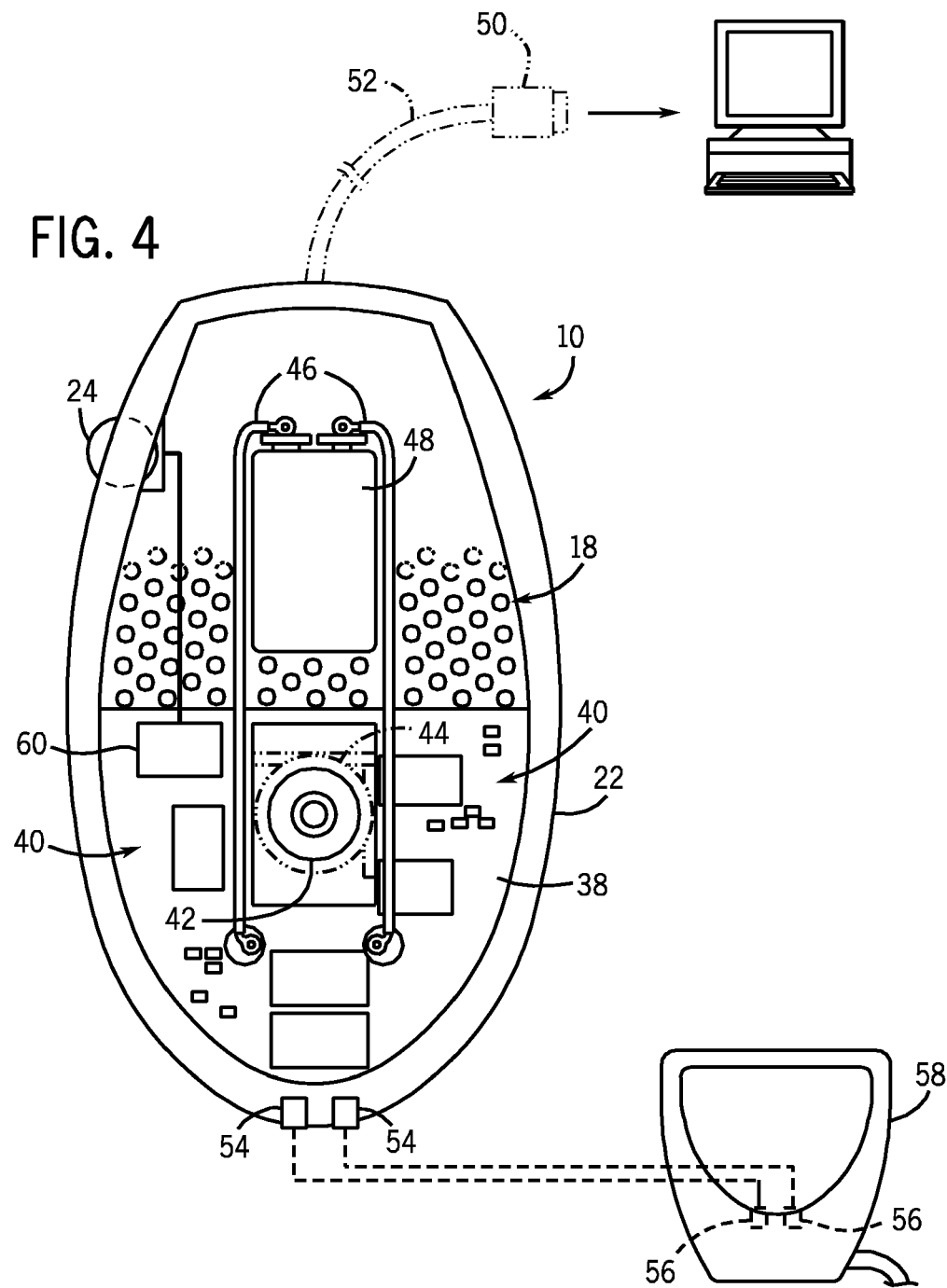
FIG. 4 is a cutaway view of the bottom of the mouse of FIG. 1.

FIG. 4 shows a cutaway view of the bottom of the peripheral 10. Peripheral 10 includes an electronics board 38 having a plurality of electronic components 40 connected thereto to provide the electrical functions of peripheral 10. An movement sensing device 42 determines planar movement of peripheral 10 relative to a surface such as a mouse pad (not shown). In a preferred embodiment, movement sensing device 42 is an optical transceiver comprising an LED emitter and a receiver to sense reflected light from the LED emitter. However, it is contemplated that movement sensing device 42 may be a ball 44 configured to optically or mechanically sense a movement direction of peripheral 10. Electrical functions of the left button 12, right button 14, and scroll wheel 16 are also provided via the plurality of electronic components 40.

A power bus 46 provides electrical power to the plurality of electronics 40 and to the plurality of infrared LEDs 18. Voltage on the power bus 46 is preferably supplied by a battery 48. Alternatively, voltage on the power bus 46 may be supplied via a USB connector 50 and cable 52 connected to a computer power supply (not shown). In a preferred embodiment, battery 48 is a rechargeable battery. A pair of contacts 54 is connected to the power bus 46 that couple with a pair of contacts 56 of a docking station 58. The docking station 58 provides recharging current to the rechargeable battery 48 to recharge the rechargeable battery 48 when the peripheral 10 is not in use.

Still referring to FIG. 4, peripheral 10 includes a controller 60 configured to control a powered state of the plurality of infrared LEDs 18. In a preferred embodiment, controller 60 is configured to control on and off powered state of the plurality of infrared LEDs 18. Switch 24 is connected to controller 60 and allows a user to input a desired powered state of the plurality of infrared LEDs 18. Controller 60 is preferably configured to control an on and off powered state of each infrared LED 18 individually. In this manner, the desired powered status may indicate that the controller 60 turn on all infrared LEDs 18, turn off all infrared LEDs 18, or control the infrared LEDs 18 according to a predefined pattern. It is contemplated, however, that controller 60 may be configured to control the powered state of a group or groups of infrared LEDs 18 as a whole.

Figure 5:
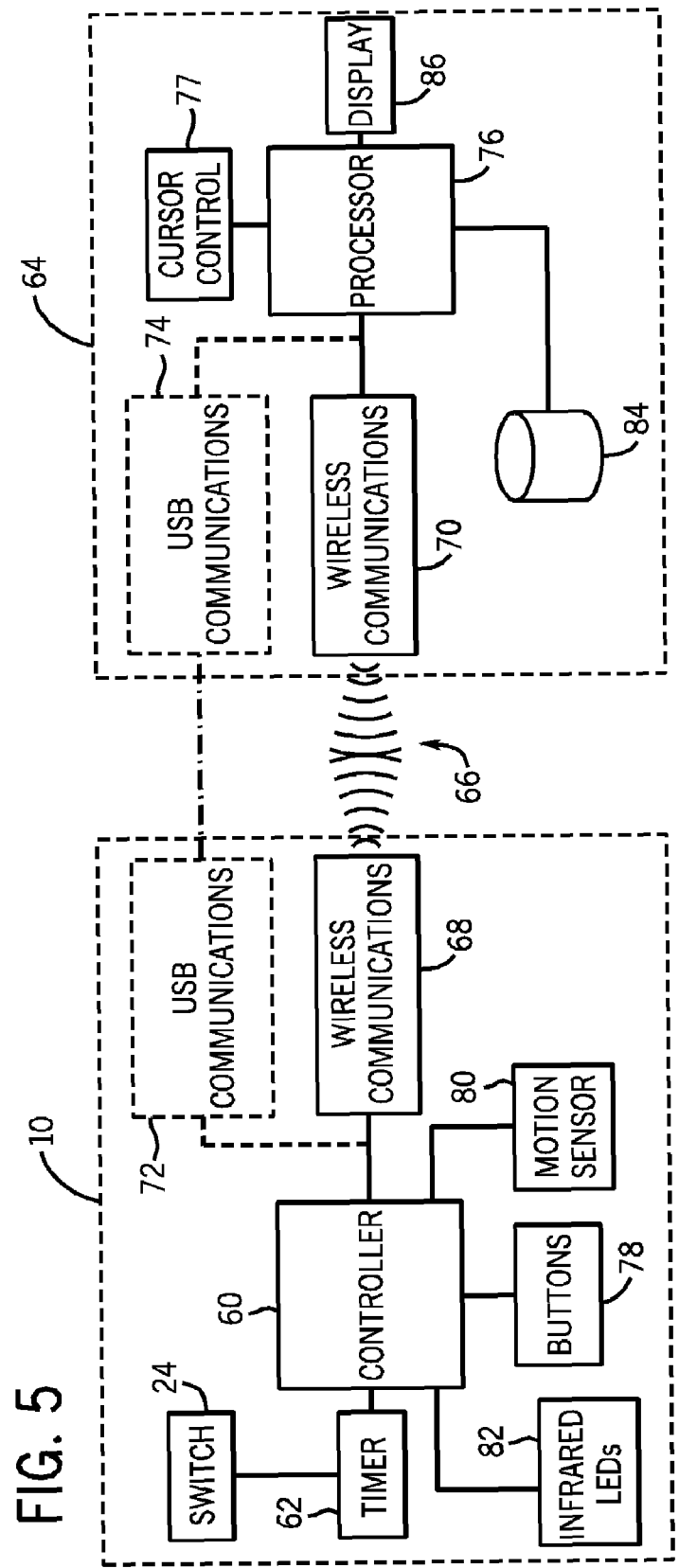
FIG. 5 is a schematic block diagram of a computer system incorporating the computer mouse of FIG. 1.

FIG. 5 shows a schematic block diagram of a computer 64 preferably connected to peripheral 10 via a wireless communications link 66 between a wireless communication circuit 68 of peripheral 10 and a wireless communication circuit 70 of computer 64. Alternatively, peripheral 10 and computer 64 may be interconnected and communicate via USB communication circuits 72, 74. Controller 60 is configured to send cursor commands via wireless communications link 66 to processor 76 of computer 64 for cursor commands such as button clicks and cursor coordinate modification. Cursor commands sent to a cursor control 77 are determined from buttons 78 and motion sensor 80.

Switch 24 preferably includes a number of intermediate positions that may be used to set a timer 62. Preferably, timer 62 controls a time in which an individual or a group of infrared LEDs 82 remains in a particular powered state. For example, timer 62 may cause controller 60 to toggle the powered state of a group of infrared LEDs 82 to an off state upon the expiration of a time threshold. Alternatively, timer 62 may set a sequence delay time between the off state of one infrared LED and the on state of another infrared LED.

Controller 60 may set timer 62 according to a particular predefined pattern. For example, the predefined pattern may include turning on a group of infrared LEDs 82 and, after timer 62 reaches a threshold, turning off the group of infrared LEDs 82. The predefined pattern may also indicate a delay time between the turning off of a group of one or more infrared LEDs 82 and the turning on of another group.

Still referring to FIG. 5, alternatively or in addition to the controller 60 controlling the powered states of the infrared LEDs 82, computer 64 may programmed to control the powered states of the infrared LEDs 82 via wireless communications link 66. A computer program stored in memory 84 may cause the computer 64 to transmit instructions to peripheral 10 causing the powered states of the infrared LEDs 82 to toggle between on and off states. Display 86 may include a graphical user interface (not shown) allowing the user to set, via keyboard or cursor input, the on state, off state, and predefined pattern of the infrared LEDs 82.

The invention, as described above, stimulates a user's hand to aid in decreasing swelling, reducing inflammation, and reducing pain. The user is able to directly re-energize the body/hand at the cellular level, thus promoting a dispersion of pain and preserving the prophylactic effects of and the dramatic increase in blood flow in the region stimulated by the infrared LEDs. By combining the functions of a computer peripheral with that of infrared therapy, computer users may reduce pain, promote healing, and provide a curative methodology to their body/hand without the need to stop working, gaming, etc. for a session of therapy.

Therefore, the invention is directed to a hand-manipulated computer peripheral including a body having a first surface portion and a second surface portion. At least one motion sensing device is positioned adjacent to the first surface portion and is configured to determine movement of the body relative to a reference. The peripheral also includes a plurality of infrared LEDs positioned adjacent to the second surface portion and configured to emit infrared light toward a hand of a user.

The invention also includes a method of manufacturing a hand-manipulated computer apparatus that includes attaching a movement detection device to a body of a hand-manipulated computer apparatus and configuring the movement detection device to monitor movement of the body relative to a surface. The method also includes attaching a bank of infrared LEDs to the body, and aligning the bank of infrared LEDs to emit infrared light toward a user's hand when the user's hand is positioned to move the body relative to the surface.

The invention is further embodied in a computer system including a computer and a mouse connected to the computer. The mouse includes a body, a movement sensing device positioned adjacent to the body and configured to detect planar translation of the body, and a plurality of infrared LEDs positioned adjacent to the body, each infrared LED oriented to emit infrared light in a direction toward a hand of a user.

The present invention has been described in terms of the preferred embodiment, and it is recognized that equivalents, alternatives, and modifications, aside from those expressly stated, are possible and within the scope of the appending claims.

What is claimed is:

1. A computer pointing device, comprising:
   a body;
   at least one motion sensing device configured to determine movement of the body relative to a reference point; and a device for emitting radiation toward a user's hand, to facilitate the treatment of repetitive stress injury when the user's hand is positioned to move the body relative to the reference point;

a controller to control the duration or intensity of emissions from the radiation-emitting device; and a switch connected to the controller and configured to communicate a desired power state to the controller.

2. The computer pointing device of claim 1, wherein the radiation comprises light radiation in the infrared spectrum.

3. The computer pointing device of claim 1, wherein the radiation-emitting device comprises a plurality of LEDs.

4. The computer pointing device of claim 3, wherein the plurality of LEDs comprises at least two arrays of LEDs which emit radiation at differing times.

5. The computer pointing device of claim 3, further comprising a timer configured to toggle the powered state of the plurality of LEDs between the on state and the off state when the timer reaches a threshold.

6. The computer pointing device of claim 1, wherein the radiation-emitting device emits a light wavelength of 880 nm.

7. The computer pointing device of claim 1, wherein the radiation-emitting device is configured to emit radiation for a predetermined duration.

8. The computer pointing device of claim 1, wherein the radiation-emitting device is configured to provide radiation emissions for a first predetermined duration, and then to stop radiation emissions for a second predetermined duration.

9. The computer pointing device of claim 1, wherein the device is a handheld computer pointing device.

10. The computer pointing device of claim 1, further comprising a communications system configured to transmit instructions from a computer to the pointing device concerning the powered state of the radiation-emitting device.

11. The computer pointing device of claim 1, further comprising a graphical user interface in electronic communication with the pointing device, enabling a user of the pointing device to set, via keyboard or cursor input, the powered state of the radiation-emitting device.

12. The computer pointing device of claim 1, wherein the at least one motion sensing device is a ball.

13. The computer pointing device of claim 1, wherein the at least one motion sensing device comprises an optical transceiver.

14. The computer pointing device of claim 1, further comprising a power bus configured to supply electrical power to the radiation-emitting device.

15. The computer pointing device of claim 14, wherein voltage on the power bus is supplied by a battery.

16. The computer pointing device of 15, wherein the battery comprises a rechargeable battery.

17. The computer pointing device of claim 16, further comprising a docking station which may be connected to the power bus for providing recharging current to the rechargeable battery.

18. A computer pointing device, comprising:

a body;

at least one motion sensing device configured to determine movement of the body relative to a reference point;

a device for emitting radiation toward a user's hand, to facilitate the treatment of repetitive stress injury when the user's hand is positioned to move the body relative to the reference point; and a communications system configured to transmit instructions from a computer to the pointing device concerning a powered state of the radiation-emitting device.

19. A computer pointing device, comprising:

a body;

at least one motion sensing device configured to determine movement of the body relative to a reference point;

a device for emitting radiation toward a user's hand, to facilitate the treatment of repetitive stress injury when the user's hand is positioned to move the body relative to the reference point; and a graphical user interface in electronic communication with the pointing device, enabling a user of the pointing device to set, via keyboard or cursor input, a powered state of the radiation-emitting device.

* * * * *